(12) United States Patent
Kawase et al.

(10) Patent No.: US 7,052,842 B2
(45) Date of Patent: May 30, 2006

(54) METHOD FOR HIGHLY SENSITIVE HYBRIDIZATION OF NUCLEIC ACIDS, AND METHOD FOR GENE ANALYSIS USING THE SAME

(75) Inventors: Mitsuo Kawase, Tita (JP); Kazunari Yamada, Nagoya (JP); Isao Miyazaki, Yokohama (JP); Chiho Matsuda, Kawasaki (JP)

(73) Assignee: NGK Insulators, Ltd., Nagoya (JP)

( * ) Notice: Subject to any disclaimer, the term of this patent is extended or adjusted under 35 U.S.C. 154(b) by 615 days.

(21) Appl. No.: 10/258,344

(22) PCT Filed: Mar. 1, 2002

(86) PCT No.: PCT/JP02/01894

§ 371 (c)(1),
(2), (4) Date: Oct. 23, 2002

(87) PCT Pub. No.: WO02/070687

PCT Pub. Date: Sep. 12, 2002

(65) Prior Publication Data
US 2003/0186266 A1    Oct. 2, 2003

(30) Foreign Application Priority Data
Mar. 7, 2001 (JP) .............................. 2001-064050

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .................. 435/6; 536/23.1, 24.3

See application file for complete search history.

(56) References Cited

U.S. PATENT DOCUMENTS

| 5,556,752 A | * | 9/1996 | Lockhart et al. ............. 435/6 |
| 5,807,522 A | * | 9/1998 | Brown et al. ................ 422/50 |
| 5,972,692 A | * | 10/1999 | Hashimoto et al. ....... 435/285.2 |
| 6,040,138 A | * | 3/2000 | Lockhart et al. ............. 435/6 |
| 6,045,996 A | * | 4/2000 | Cronin et al. ............... 435/6 |
| 6,344,316 B1 | * | 2/2002 | Lockhart et al. ............. 435/6 |

FOREIGN PATENT DOCUMENTS

| EP | 0 852 263 A1 | 7/1998 |
| JP | A 5-91896 | 4/1993 |
| JP | A 8-191700 | 7/1996 |
| JP | A 2000-325099 | 11/2000 |

OTHER PUBLICATIONS

Yoshinari Fukuda, "Southern Northern Hybridization Ho", Medical Technology, vol. 26, No. 3, pp. 239-244, 1998, abstract only.
Yoshinari Fukuda, "Southern Northern Hybridization Ho", Medical Technology, vol.26 No. 3, pp. 239-244, 1998.

* cited by examiner

*Primary Examiner*—Ethan Whisenant
(74) *Attorney, Agent, or Firm*—Oliff & Berridge, PLC

(57) ABSTRACT

A method for hybridizing nucleic acids, which includes an annealing step of preparing a first single stranded nucleic acid fragment immobilized on a surface of an immobilizing material and a second single stranded nucleic acid fragment labeled with fluorescence or radioisotope and forming a complementary double strand from the first single stranded nucleic acid fragment and the second single stranded nucleic acid fragment, and an enzyme treatment step. In the annealing step, the complementary double strand is formed by performing a temperature gradient processing performed from a high temperature area to a low temperature area, and in the enzyme treatment step, a noncomplementary nucleic acid portion contained in the complementary double stand is recognized and cleaved by adding endonuclease. This method has high measurement sensitivity and the operation is simple.

6 Claims, No Drawings

METHOD FOR HIGHLY SENSITIVE HYBRIDIZATION OF NUCLEIC ACIDS, AND METHOD FOR GENE ANALYSIS USING THE SAME

TECHNICAL FIELD

The present invention relates to a method for highly sensitive hybridization of nucleic acids and a method for gene analysis using the same.

BACKGROUND ART

A test method using a DNA sequencer or the like is practically used for the diagnosis of genetic diseases caused by genetic malformation or diseases caused by DNA mutation or the like such as various types of cancer. On the other hand, the decoding of the genomic base sequences of various types of organisms has progressed, and based on the findings, research and development aiming at analyzing gene function have further vigorously been progressing.

Incidentally, for analysis of gene function, there is required the development of techniques of efficiently measuring and testing individual difference or mutation of a genetic sequence, the frequency of gene expression in a cell, etc. Among such techniques, as one of methods for testing cancer or the like, there is known a method for examining the expression of a specific gene, which comprises adding a test sample consisting of a DNA fragment extracted from a subject and labeled with fluorescence or radioisotope onto a DNA microarray on which a given target DNA fragment is mounted in advance, performing hybridization, identifying and recognizing fluorescent- or radioisotope-labeling on a specific spot, so as to examine whether or not the specific gene expresses in the test sample.

In a step of forming a complementary double strand from a DNA fragment immobilized on a microarray and a DNA probe labeled with fluorescence or radioisotope (hereinafter, referred to as an "annealing step"), various conditions such as temperature, pH and salt concentration are set as appropriate depending on the base composition of used DNA. For example, a temperature condition is set using the melting temperature (hereinafter, referred to as "Tm") of DNA as an indicator.

Generally, where DNA has a fixed length, as the GC content represented by the total of the content rates of guanine and cytosine that are the types of bases constituting DNA increases, the Tm value increases. Moreover, the temperature of annealing differs depending on the length of the repeat sequence of DNA and the structural complexity of repeat number. Accordingly, the optimal temperature of annealing is specific for a DNA fragment, and the optimal temperature of annealing differs depending on a DNA probe used.

Furthermore, factors of determining conditions for annealing include pH, salt concentration or the like other than the above described temperature, but in any cases, the optimal conditions differ depending on the type of a DNA fragment used. That is to say, when multiple kinds of DNA probes are used, it is difficult to undifferentiatedly determine the conditions for annealing. Accordingly, in many cases, it is common that hybridization is carried out under conditions such as a low temperature, neutral pH and a high salt concentration, where annealing can be performed relatively easily, and then gene expression is analyzed.

However, since even DNAs having low complementarity are annealed with each other under the above described annealing conditions, there is a need to eliminate double stranded DNA having low complementarity in a washing operation following the annealing. Therefore, there may occur problems that a washing performed under stringent conditions results in poor detection sensitivity or the like.

In contrast, if a washing operation is carried out moderately to increase detection sensitivity, the noise signal from background increases, the number of pseudo-positive increases, and thereby it becomes difficult to perform an accurate test and analysis. So, detection sensitivity may be lowered depending on used DNA probes and test samples, and therefore the development of a hybridization method having higher detection sensitivity has been desired for highly sensitive gene expression analysis.

The present invention has been made to solve such problems of the prior art, and it is an object of the present invention to provide a method for hybridizing nucleic acids, which has high measurement sensitivity with simple operation, and a method for gene analysis using the above method for hybridizing nucleic acids.

DISCLOSURE OF THE INVENTION

That is to say, according to the present invention, there is provided a method for hybridizing nucleic acids, which comprises an annealing step of preparing a first single stranded nucleic acid fragment immobilized on the surface of an immobilizing material and a second single stranded nucleic acid fragment labeled with fluorescence or radioisotope and forming a complementary double strand from the first single stranded nucleic acid fragment and the second single stranded nucleic acid fragment, and an enzyme treatment step, characterized in that said complementary double strand is formed by a temperature gradient processing from a high temperature area to a low temperature area in said annealing step, and an endonuclease is added to recognize and remove a noncomplementary nucleic acid portion contained in said complementary double stand in said enzyme treatment step.

Moreover, in the present invention, it is preferable that, in the above described annealing step, a pH gradient processing is performed from a high pH area to a low pH area instead of the temperature gradient processing from a high temperature area to a low temperature area.

Furthermore, in the present invention, it is preferable that, in the above described annealing step, a salt concentration gradient processing is performed from a low salt concentration area to a high salt concentration area instead of the temperature gradient processing from a high temperature area to a low temperature area.

On the other hand, according to the present invention, there is provided a method for gene analysis, characterized in that there is used any one of the above-described methods for hybridizing nucleic acids.

BEST MODE FOR CARRYING OUT THE INVENTION

The embodiments of the present invention will be explained below. However, the following embodiments are not intended to limit the scope of the present invention, and it should be understood that various changes, modifications and so on can be made as appropriate based on the common knowledge of a person skilled in the art without departing from the spirit of the present invention.

In the method for hybridizing nucleic acids of the present invention, firstly, a first single stranded nucleic acid fragment, which is previously immobilized on the surface of an immobilizing material, and a second single stranded nucleic acid fragment labeled with fluorescence or radioisotope, are prepared. Secondly, while performing a temperature gradient processing from a high temperature area to a low temperature area, the first single stranded nucleic acid fragment and the second single stranded nucleic acid fragment are subjected to annealing (an annealing step) to form a complementary double strand. Subsequently, by adding endonuclease, a noncomplementary nucleic acid portion contained in the complementary double stand formed in the above described annealing step is recognized, cleaved, and eliminated (an enzyme treatment step).

Thus, in the above described annealing step, a temperature gradient processing is performed from a high temperature area to a low temperature area, so that the annealing is started under a high temperature condition where it is hard to perform annealing, and then the processing temperature is decreased gradually. Accordingly, when compared with the previous methods in which annealing is performed at a specific temperature, it is possible to eliminate nonspecific annealing.

In the above described step, there may be cases where nonspecific annealing occurs. Thus, by adding endonuclease into a reaction system in the following enzyme treatment step, a non-paired base pair portion that is a noncomplementary portion contained in a complementary double strand is recognized, cleaved, and eliminated. By this processing, it is possible to measure and detect only a portion forming a completely complementary double strand.

Moreover, by combining the enzyme treatment step with the above described annealing step of performing a temperature gradient processing, it is possible to realize high detection sensitivity in the following analysis.

Examples of an immobilizing material which is preferably used herein include a reactor comprising a suitable well such as a polystyrene substrate, a glass substrate which is surface-treated to impart an affinity for nucleic acids, and a microtiter plate, or a membrane such as nitrocellulose and nylon.

Furthermore, examples of the first and second single stranded nucleic acid fragments, which are preferably used, generally include a cloned DNA fragment, an amplified DNA fragment amplified by PCR method, an RNA fragment, cDNA, oligonucleotide, etc. Since the PCR amplification method is known to a person skilled in the art, it is not described herein. It should be noted that the PCR amplification method is described in, for example, Innis M., D. H. Gelfand, J. J. Sninsky and T. White, PCR Protocols: A Guide to Methods and Applications, Academic Press N. Y., N. Y., 1990, which can be referred to as necessary.

Still further, endonuclease used in the enzyme treatment step can be any endonuclease in such an extent that the enzyme recognizes and cleaves a noncomplementary nucleic acid portion comprised in a complementary double strand. The above described high detection sensitivity can be achieved by the addition of such an endonuclease. Examples of an endonuclease preferably used include a DNA repair enzyme such as uvrABC exonuclease.

What is more, in the method for hybridizing nucleic acids of the present invention, it is also preferable to perform a pH gradient processing from a high pH area to a low pH area, instead of the temperature gradient processing performed from a high temperature area to a low temperature area in the above described annealing step. One condition in the annealing step, pH, is a factor of determining the easiness to perform annealing. That is, annealing is started under a high pH condition where it is hard to perform the annealing, and then the processing pH is decreased gradually. Accordingly, when compared with the previous methods in which annealing is performed at a specific pH value, it is possible to eliminate nonspecific annealing.

Herein, any type of commonly used acidic aqueous solution can be used to decrease pH, but hydrochloric acid, phosphoric acid, dibasic sodium phosphate or the like can preferably be used. Of these, hydrochloric acid can preferably be used. It is used as appropriate within a concentration range capable of controlling pH at 12 to 7, and then the pH may gradually be decreased.

Moreover, in the method for hybridizing nucleic acids of the present invention, it is also preferable to perform a salt concentration gradient processing from a low salt concentration area to a high salt concentration area, instead of the temperature gradient processing performed from a high temperature area to a low temperature area in the above described annealing step. One condition in the annealing step, salt concentration, is a factor of determining the easiness to perform annealing. That is, annealing is started under a low salt concentration condition where it is hard to perform the annealing, and then the processing salt concentration is increased gradually. Accordingly, when compared with the previous methods in which annealing is performed in a specific salt concentration area, it is possible to eliminate nonspecific annealing.

Examples of a salt preferably used herein to determine salt concentration include inorganic salts such as sodium chloride, potassium chloride and sodium sulfate, and of these, sodium chloride is preferably used. Using these salts, salt concentration may gradually be increased, for example, within a concentration range of 15 mM to 3 M.

Moreover, the parameter in each of the above described temperature gradient, pH gradient, and salt concentration gradient may be altered in a stepwise manner (stepwise), or may be altered in a gradient manner. Furthermore, in addition to the individual alteration of each parameter, two or more of these parameters may also be altered together in combination.

To use the above described nucleic acid hybridization method in a gene analysis method, there may be used fluorescence such as FAM, Rhodamine, Cy3 and Cy5, oligonucleotide having a 5'-end labeled with radioisotope, DNA labeled with fluorescence or radioisotope by nick-translation, etc. The analysis may be carried out according to common techniques, and in the case of DNA labeled with fluorescence for example, the analysis is carried out using a fluorescence microarray scanner or the like. Specifically, it may be carried out according to the method described in the above mentioned Kosuke Tashiro et al., Saibo Kogaku (Cell Technology), Vol. 18, No. 7 (1999): 1050–1056, etc.

The present invention will be explained further in detail below, using examples and comparative examples. However, it is needless to say that the following examples are not intended to limit the scope of the invention.

EXAMPLES

1. Blotting

Using 200 ng of 2961 bp fragment of pBluescript II KS shown in SEQ ID NO:1 (this sequence shows all nucleotide sequence), blotting was carried out on a Hybond N+ (Amersham Pharmacia) membrane according to common techniques.

2. Preparation of Probe

A 20 bp fragment of pBK2-15-FAM shown in SEQ ID NO:2 (oligonucleotide fluorescently labeled with FAM, Lifetech) and a 20 bp fragment of pBK2-306-Rho shown in SEQ ID NO:3 (oligonucleotide fluorescently labeled with Rhodamine, Lifetech) were prepared and used. The GC contents of pBK2-15-FAM and pBK2-306-Rho were 10% and 50%, respectively.

3. Temperature Gradient Conditions (Examples 1 to 3)

After blotting, the membrane was placed in a hybridization bag and subjected to a prehybridization at 42° C. for 2 hours in a prehybridization cocktail (5×SSPE, 5×Denhart's solution, 0.5% SDS, 100 µg Salmon sperm DNA). After that, 100 ng each of only the pBK2-15-FAM, only the pBK2-306-Rho, and both the pBK2-15-FAM and the pBK2-306-Rho was added thereto (Examples 1 to 3), and each mixture was shaken at 55° C. for 2 hours and then at 40° C. for 2 hours under conditions of pH 7.4 and 750 mM NaCl.

4. pH Gradient Conditions (Examples 4 to 6)

After blotting, the membrane was placed in a hybridization bag and subjected to a prehybridization at 42° C. for 2 hours in a prehybridization cocktail (5×SSPE, 5×Denhart's solution, 0.5% SDS, 100 µg Salmon sperm DNA, pH 11). After that, 100 ng each of only the pBK2-15-FAM, only the pBK2-306-Rho, and both the pBK2-15-FAM and the pBK2-306-Rho was added thereto (Examples 4 to 6). Each mixture was shaken for 2 hours under conditions of 42° C. and 750 mM NaCl. Subsequently, 1N HCl was added thereto, and the mixture was shaken at pH 10 for 2 hours, at pH 9 for 2 hours, and at pH 8 for 2 hours.

5. Salt Concentration Gradient Conditions (Examples 7 to 9)

After blotting, the membrane was placed in a hybridization bag and subjected to a prehybridization at 42° C. for 2 hours in a prehybridization cocktail (0.1×SSPE, 5×Denhart's solution, 0.5% SDS, 100 µg Salmon sperm DNA). After that, 100 ng each of only the pBK2-15-FAM, only the pBK2-306-Rho, and both the pBK2-15-FAM and the pBK2-306-Rho was added thereto (Examples 7 to 9). Under conditions of 42° C. and pH 7.4, NaCl was added to each mixture, and the mixture containing 20 mM at final concentration of salts was shaken for 2 hours, and then the mixture containing 200 mM at final concentration of salts was shaken for 2 hours.

6. Washing of Membrane and Nuclease Treatment

The membrane was lightly rinsed with 2×SSPE, and then transferred into 1 ml of buffer solution (50 mM KAc, 20 mM Tris-AcOH, 10 mM MgAc$_2$, 1 mM DTT). Then, 50 units of T7 Endonuclease I (New England Biolabs) was added thereto, and the mixture was reacted at 37° C. for 15 minutes followed by rinsing with a washing solution (2×SSPE).

7. Measurement

Using a molecular imager FX (Bio-Rad), the fluorescence amount of FAM and/or Rhodamine was measured. Results are shown in Table 1.

COMPARATIVE EXAMPLES

Annealing was carried out in the same manner as in the above described examples with the exception that the gradient condition of each of temperature, pH, and salt concentration was not set for the annealing (Comparative Examples 1 to 3). After that, the membrane was washed twice at 42° C. for 15 minutes using a solution 1 (2×SSPE, 0.1% SDS), and then washed once at 42° C. for 15 minutes using a solution 2 (1×SSPE, 0.1% SDS). Then, the fluorescence amount of FAM and/or Rhodamine was measured. Similarly, results are shown in Table 1.

TABLE 1

| | Fluorescent labeling | | Temperature (° C.) | pH | Salt concentration nM | Addition of endonuclease | Relative intensity | |
|---|---|---|---|---|---|---|---|---|
| | FAM | Rhodamine | | | | | FAM | Rhodamine |
| Example 1 | + | − | 55→40 | 7.4 | 750 | + | 3802 | 498 |
| Example 2 | − | + | 55→40 | 7.4 | 750 | + | 524 | 2879 |
| Example 3 | + | + | 55→40 | 7.4 | 750 | + | 5124 | 3154 |
| Example 4 | + | − | 42 | 11→8 | 750 | + | 1587 | 587 |
| Example 5 | − | + | 42 | 11→8 | 750 | + | 682 | 1882 |
| Example 6 | + | + | 42 | 11→8 | 750 | + | 2536 | 2251 |
| Example 7 | + | − | 42 | 7.4 | 20→200 | + | 2847 | 358 |
| Example 8 | − | + | 42 | 7.4 | 20→200 | + | 258 | 2468 |
| Example 9 | + | + | 42 | 7.4 | 20→200 | + | 3584 | 2687 |
| Comparative Example 1 | + | + | 40 | 7.4 | 500 | − | 925 | 896 |
| Comparative Example 2 | + | + | 40 | 7.4 | 500 | − | 1287 | 1785 |
| Comparative Example 3 | + | + | 40 | 7.4 | 500 | − | 1058 | 879 |

(Discussion)

As is clear from the above results, it is found that the method of the present invention provides measurement sensitivity significantly higher than that in Comparative Examples. Moreover, the washing operation is simple, and it could be confirmed that the present invention has an advantage.

INDUSTRIAL APPLICABILITY

As stated above, according to the method for hybridizing nucleic acids of the present invention, nonspecific annealing is unlikely to occur in an annealing step because the gradient processing of each of temperature, pH, and salt concentration is performed. Moreover, since an endonuclease treatment is carried out in the following enzyme treatment step, it is possible to realize the collection of highly reliable data and high measurement sensitivity.

Further, by using this hybridization method, a method for gene analysis capable of measuring with higher sensitivity is provided.

The invention claimed is:

1. A method for hybridizing nucleic acids, which comprises an annealing step of preparing a first single stranded nucleic acid fragment immobilized on a surface of an immobilizing material and a second single stranded nucleic acid fragment labeled with a fluorophore or radioisotope and forming a complementary double strand from the first single stranded nucleic acid fragment and the second single stranded nucleic acid fragment, and an enzyme treatment step, characterized in that said complementary double strand is formed by a temperature gradient processing from a high temperature area to a low temperature area in said annealing step, and an endonuclease is added to recognize and remove a non- complementary nucleic acid portion contained in said complementary double strand in said enzyme treatment step.

2. A method for hybridizing nucleic acids, which comprises an annealing step of preparing a first single stranded nucleic acid fragment immobilized on a surface of an immobilizing material and a second single stranded nucleic acid fragment labeled with a fluorophore or radioisotope and forming a complementary double strand from the first single stranded nucleic acid fragment and the second single stranded nucleic acid fragment, and an enzyme treatment step, characterized in that said complementary double strand is formed by a pH gradient processing from a high pH area to a low pH area in said annealing step, and an endonuclease is added to recognize and remove a non-complementary nucleic acid portion contained in said complementary double strand in said enzyme treatment step.

3. A method for hybridizing nucleic acids, which comprises an annealing step of preparing a first single stranded nucleic acid fragment immobilized on a surface of an immobilizing material and a second single stranded nucleic acid fragment labeled with a fluorophore or radioisotope and forming a complementary double strand from the first single stranded nucleic acid fragment and the second single stranded nucleic acid fragment, and an enzyme treatment step, characterized in that said complementary double strand is formed by a salt concentration gradient processing from a low salt concentration area to a high salt concentration area in said annealing step, and an endonuclease is added to recognize and remove a non-complementary nucleic acid portion contained in said complementary double strand in said enzyme treatment step.

4. A method for the analysis of a nucleic acid, comprising
   (i) a method for hybridizing nucleic acids according to claim 1 and
   (ii) assessing the results of step (i) whereby said nucleic acid is analyzed.

5. A method for the analysis of a nucleic acid, comprising
   (i) a method for hybridizing nucleic acids according to claim 2 and
   (ii) assessing the results of step (i) whereby said nucleic acid is analyzed.

6. A method for the analysis of a nucleic acid, comprising
   (i) a method for hybridizing nucleic acids according to claim 3 and
   (ii) assessing the results of step (i) whereby said nucleic acid is analyzed.

* * * * *

SEQUENCE LISTING

<160> NUMBER OF SEQ ID NOS: 3
<210> SEQ ID NO 1
<211> LENGTH: 2961
<212> TYPE: DNA
<213> ORGANISM: Artificial Sequence
<220> FEATURE:
<223> OTHER INFORMATION: fragment of pBluescript II KS

<400> SEQUENCE: 1

| | | | | | |
|---|---|---|---|---|---|
| ctaaattgta | agcgttaata | ttttgttaaa | attcgcgtta | aattttgtt | aaatcagctc | 60 |
| attttttaac | caataggccg | aaatcggcaa | aatcccttat | aaatcaaaag | aatagaccga | 120 |
| gataggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggt | tttcccagt | cacgacgttg | 600 |
| taaaacgacg | gccagtgagc | gcgcgtaata | cgactcacta | tagggcgaat | tggagctcca | 660 |
| ccgcggtggc | ggccgctcta | gaactagtgg | atccccggg | ctgcaggaat | tcgatatcaa | 720 |
| gcttatcgat | accgtcgacc | tcgagggggg | gcccggtacc | cagcttttgt | tccctttagt | 780 |
| gagggttaat | tgcgcgcttg | gcgtaatcat | ggtcatagct | gtttcctgtg | tgaaattgtt | 840 |
| atccgctcac | aattccacac | aacatacgag | ccggaagcat | aaagtgtaaa | gcctggggtg | 900 |
| cctaatgagt | gagctaactc | acattaattg | cgttgcgctc | actgcccgct | ttccagtcgg | 960 |
| gaaacctgtc | gtgccagctg | cattaatgaa | tcggccaacg | cgcggggaga | ggcggtttgc | 1020 |
| gtattgggcg | ctcttccgct | tcctcgctca | ctgactcgct | gcgctcggtc | gttcggctgc | 1080 |
| ggcgagcggt | atcagctcac | tcaaaggcgg | taatacggtt | atccacagaa | tcagggata | 1140 |
| acgcaggaaa | gaacatgtga | gcaaaaggcc | agcaaaaggc | caggaaccgt | aaaaaggccg | 1200 |
| cgttgctggc | gtttttccat | aggctccgcc | ccctgacga | gcatcacaaa | aatcgacgct | 1260 |
| caagtcagag | gtggcgaaac | ccgacaggac | tataaagata | ccaggcgttt | cccctggaa | 1320 |
| gctccctcgt | gcgctctcct | gttccgaccc | tgccgcttac | cggatacctg | tccgcctttc | 1380 |
| tcccttcggg | aagcgtggcg | ctttctcata | gctcacgctg | taggtatctc | agttcggtgt | 1440 |
| aggtcgttcg | ctccaagctg | ggctgtgtgc | acgaaccccc | cgttcagccc | gaccgctgcg | 1500 |
| ccttatccgg | taactatcgt | cttgagtcca | acccggtaag | acacgactta | tcgccactgg | 1560 |
| cagcagccac | tggtaacagg | attagcagag | cgaggtatgt | aggcggtgct | acagagttct | 1620 |
| tgaagtggtg | gcctaactac | ggctacacta | gaaggacagt | atttggtatc | tgcgctctgc | 1680 |
| tgaagccagt | taccttcgga | aaaagagttg | gtagctcttg | atccggcaaa | caaaccaccg | 1740 |
| ctggtagcgg | tggttttttt | gtttgcaagc | agcagattac | gcgcagaaaa | aaaggatctc | 1800 |
| aagaagatcc | tttgatcttt | tctacggggt | ctgacgctca | gtggaacgaa | aactcacgtt | 1860 |
| aagggatttt | ggtcatgaga | ttatcaaaaa | ggatcttcac | ctagatcctt | ttaaattaaa | 1920 |
| aatgaagttt | taaatcaatc | taaagtatat | atgagtaaac | ttggtctgac | agttaccaat | 1980 |

```
                                           -continued gcttaatcag tgaggcacct atctcagcga tctgtctatt tcgttcatcc atagttgcct    2040
gactccccgt cgtgtagata actacgatac gggagggctt accatctggc cccagtgctg    2100
caatgatacc gcgagaccca cgctcaccgg ctccagattt atcagcaata aaccagccag    2160
ccggaagggc cgagcgcaga agtggtcctg caactttatc cgcctccatc cagtctatta    2220
attgttgccg ggaagctaga gtaagtagtt cgccagttaa tagtttgcgc aacgttgttg    2280
ccattgctac aggcatcgtg gtgtcacgct cgtcgtttgg tatggcttca ttcagctccg    2340
gttcccaacg atcaaggcga gttacatgat cccccatgtt gtgcaaaaaa gcggttagct    2400
ccttcggtcc tccgatcgtt gtcagaagta agttggccgc agtgttatca ctcatggtta    2460
tggcagcact gcataattct cttactgtca tgccatccgt aagatgcttt tctgtgactg    2520
gtgagtactc aaccaagtca ttctgagaat agtgtatgcg gcgaccgagt tgctcttgcc    2580
cggcgtcaat acgggataat accgcgccac atagcagaac tttaaaagtg ctcatcattg    2640
gaaaacgttc ttcggggcga aaactctcaa ggatcttacc gctgttgaga tccagttcga    2700
tgtaacccac tcgtgcaccc aactgatctt cagcatcttt tactttcacc agcgtttctg    2760
ggtgagcaaa aacaggaagg caaaatgccg caaaaaaggg aataagggcg acacggaaat    2820
gttgaatact catactcttc cttttcaat attattgaag catttatcag ggttattgtc     2880
tcatgagcgg atacatattt gaatgtattt agaaaaataa acaaatagggg gttccgcgca   2940 catttcccccg aaaagtgcca c                                             2961

<210> SEQ ID NO 2
<211> LENGTH: 20
<212> TYPE: DNA
<213> ORGANISM: Artificial Sequence
<220> FEATURE:
<223> OTHER INFORMATION: fragment of pBK2-15-FAM

<400> SEQUENCE: 2 ttaatattt gttaaaattc                                                 20

<210> SEQ ID NO 3
<211> LENGTH: 20
<212> TYPE: DNA
<213> ORGANISM: Artificial Sequence
<220> FEATURE:
<223> OTHER INFORMATION: fragment of pBK2-306-Rho

<400> SEQUENCE: 3
gatttagagc ttgacgggga                                                20
```